US 12,284,044 B2

(12) United States Patent
Wang et al.

(10) Patent No.: US 12,284,044 B2
(45) Date of Patent: *Apr. 22, 2025

(54) METHOD AND APPARATUS FOR EFFICIENTLY UTILIZING HARQ PROCESSES FOR SEMI-PERSISTENT AND DYNAMIC DATA TRANSMISSIONS

(71) Applicant: InterDigital Patent Holdings, Inc., Wilmington, DE (US)

(72) Inventors: Jin Wang, Princeton, NJ (US); Guodong Zhang, Woodbury, NY (US)

(73) Assignee: InterDigital Patent Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/531,061

(22) Filed: Dec. 6, 2023

(65) Prior Publication Data
US 2024/0106580 A1 Mar. 28, 2024

Related U.S. Application Data

(63) Continuation of application No. 18/074,223, filed on Dec. 2, 2022, now Pat. No. 11,888,629, which is a (Continued)

(51) Int. Cl.
*H04L 1/1867* (2023.01)
*H04L 1/1812* (2023.01)
(Continued)

(52) U.S. Cl.
CPC .......... *H04L 1/1887* (2013.01); *H04L 1/1812* (2013.01); *H04L 1/1822* (2013.01);
(Continued)

(58) Field of Classification Search
CPC ... H04L 1/1887; H04L 1/1812; H04L 1/1822; H04L 1/1896; H04L 5/0055; H04L 1/18;
(Continued)

(56) References Cited

U.S. PATENT DOCUMENTS 7,484,000 B2  1/2009  Jiang
8,134,924 B2  3/2012  Li et al.
(Continued)

FOREIGN PATENT DOCUMENTS

CN  101106439 A  1/2008
TW  200303660 A  9/2003
(Continued)

OTHER PUBLICATIONS

3rd Generation Partnership Project (3GPP), R1-081020, "Detail on Mapping between ACK/NACK Index and CCE Index", NEC Group, 3GPP TSG RAN WG1 Meeting #52, Sorrento, Italy, Feb. 11-15, 2008, 4 pages.

(Continued)

*Primary Examiner* — James C Kerveros
(74) *Attorney, Agent, or Firm* — Flaster Greenberg, P.C.

(57) ABSTRACT

A method and apparatus are disclosed for efficient hybrid automatic repeat request (HARQ) process utilization for semi-persistent and dynamic data transmissions, wherein a reserved HARQ process identification (ID) can be reused. A subset of a plurality of HARQ process IDs is reserved to use for a semi-persistent allocation, and data is transmitted based on the semi-persistent allocation. A dynamic allocation is received via a physical downlink control channel (PDCCH). At least one of the reserved HARQ process IDs is selectively used for transmitting data based on the dynamic allocation.

20 Claims, 3 Drawing Sheets

US 12,284,044 B2
Page 2

Related U.S. Application Data continuation of application No. 16/406,826, filed on May 8, 2019, now Pat. No. 11,558,153, which is a continuation of application No. 14/605,562, filed on Jan. 26, 2015, now Pat. No. 10,305,641, which is a continuation of application No. 13/735,494, filed on Jan. 7, 2013, now Pat. No. 8,943,378, which is a continuation of application No. 12/399,174, filed on Mar. 6, 2009, now Pat. No. 8,386,872.

(60) Provisional application No. 61/035,273, filed on Mar. 10, 2008.

(51) Int. Cl.
  *H04L 1/1822* (2023.01)
  *H04L 5/00* (2006.01)
  *H04W 8/26* (2009.01)
  *H04W 28/04* (2009.01)
  *H04W 28/26* (2009.01)
  *H04W 72/04* (2023.01)
  *H04W 72/23* (2023.01)

(52) U.S. Cl.
  CPC .......... *H04L 1/1896* (2013.01); *H04L 5/0055* (2013.01); *H04W 72/23* (2023.01); *H04W 8/26* (2013.01); *H04W 28/04* (2013.01); *H04W 28/26* (2013.01); *H04W 72/04* (2013.01)

(58) Field of Classification Search
  CPC ....... H04W 72/23; H04W 8/26; H04W 28/04; H04W 28/26; H04W 72/04; A61P 25/00
  USPC ......................................................... 370/329
  See application file for complete search history.

(56) References Cited

U.S. PATENT DOCUMENTS

| | | | |
|---|---|---|---|
| 8,307,250 B2 | 11/2012 | Cai et al. | |
| 8,320,341 B2 | 11/2012 | Malkamaki et al. | |
| 8,359,509 B2 | 1/2013 | Womack et al. | |
| 8,386,872 B2* | 2/2013 | Wang | A61P 25/00 |
| | | | 714/749 |
| 8,687,541 B2 | 4/2014 | Lohr et al. | |
| 9,445,167 B2 | 9/2016 | You et al. | |
| 10,075,913 B2 | 9/2018 | Ohta et al. | |
| 2002/0172208 A1 | 11/2002 | Malkamaki | |
| 2003/0147348 A1 | 8/2003 | Jiang | |
| 2005/0073978 A1 | 4/2005 | Kim et al. | |
| 2005/0249120 A1 | 11/2005 | Heo et al. | |
| 2006/0062140 A1 | 3/2006 | Sudo | |
| 2008/0059859 A1 | 3/2008 | Marinier et al. | |
| 2008/0117891 A1* | 5/2008 | Damnjanovic | H04W 72/04 |
| | | | 370/345 |
| 2008/0205348 A1 | 8/2008 | Malladi | |
| 2008/0232315 A1 | 9/2008 | Bachl et al. | |
| 2009/0040928 A1 | 2/2009 | Wang et al. | |
| 2009/0046639 A1* | 2/2009 | Cai | H04L 47/801 |
| | | | 370/352 |
| 2009/0103500 A1* | 4/2009 | Malkamaki | H04L 1/1854 |
| | | | 370/336 |
| 2009/0245194 A1 | 10/2009 | Damnjanovic et al. | |
| 2009/0287976 A1 | 11/2009 | Wang et al. | |
| 2010/0017671 A1 | 1/2010 | Cai et al. | |
| 2010/0081443 A1 | 4/2010 | Meyer et al. | |
| 2010/0085927 A1 | 4/2010 | Torsner et al. | |
| 2010/0284364 A1 | 11/2010 | You et al. | |
| 2016/0270064 A1 | 9/2016 | Dinan | |
| 2017/0272228 A1 | 9/2017 | Boariu et al. | |
| 2017/0310429 A1 | 10/2017 | Wang et al. | |
| 2017/0367089 A1 | 12/2017 | Terry et al. | |
| 2017/0373802 A1 | 12/2017 | Bergstrom et al. | |

FOREIGN PATENT DOCUMENTS

| | | |
|---|---|---|
| TW | 200939685 A | 9/2009 |
| WO | WO 2008/114222 A2 | 9/2008 |
| WO | WO 2008/115134 A2 | 9/2008 |
| WO | WO 2009/020363 A1 | 2/2009 |
| WO | WO 2010/030806 A1 | 3/2010 |

OTHER PUBLICATIONS

3rd Generation Partnership Project (3GPP), R2-071742, "UL VoIP Capacity for Semi-Persistent Scheduling and Group Scheduling", Nokia Siemens Networks, 3GPP TSG-RAN WG2 Meeting #58, Kobe, Japan, May 7-11, 2007, 7 pages.

3rd Generation Partnership Project (3GPP), R2-080139, "Control of Semi-Persistent Scheduling by L1/L2 Control Channel", ETRI, 3GPP TSG RAN WG2 #60bis, Sevilla, Spain, Jan. 14-18, 2008, pp. 1-3.

3rd Generation Partnership Project (3GPP), R2-080342, "HARQ Process ID's for DL Persistent Scheduling", Nortel, 3GPP TSG RAN WG2 #60bis, Sevilla, Spain, January 1418, 2008, pp. 1-6.

3rd Generation Partnership Project (3GPP), R2-080683, "Persistent Scheduling for DL", Nokia Siemens Network, 3GPP TSG-RAN WG2 Meeting #61, Sorrento, Italy, Feb. 11-15, 2008, 6 pages.

3rd Generation Partnership Project (3GPP), R2-080828, "HARO Retransmissions for the DL Persistent Scheduling", Samsung, 3GPP TSG RAN WG2 #61, Sorrento, Italy, Feb. 11-15, 2008, 2 pages.

3rd Generation Partnership Project (3GPP), R2-081072, "Allocation of Semi-Persistent Resources", Qualcomm Europe, 3GPP TSG-RAN WG 2 Meeting #61, Sorrento, Italy, Feb. 11-15, 2008, pp. 1-2.

3rd Generation Partnership Project (3GPP), R2-081081, "Re-Transmission of Persistent Scheduling", LG Electronics Inc., 3GPP TSG-RAN WG2 #61, Sorrento, Italy, Feb. 11-15, 2008, pp. 1-3.

3rd Generation Partnership Project (3GPP), R2-082302, R2-081542, "Persistent Scheduling for DL", Nokia Siemens Networks, 3GPP TSG-RAN WG2 Meeting #62, Kansas City, USA, May 5-9, 2008, 6 pages.

3rd Generation Partnership Project (3GPP), TDOC R2-073386, "HARO Retransmissions for the DL Persistent Scheduling", Samsung, 3GPP TSG-RAN2 Meeting #59, Athens, Greece, Aug. 20-24, 2007, 2 pages.

3rd Generation Partnership Project (3GPP), TS 25.321 V2.0.0, "Technical Specification Group (TSG) RAN, Working Group 2(WG2), MAC Protocol Specification", Apr. 1999, pp. 1-39.

3rd Generation Partnership Project (3GPP), TS 25.321 V3.17 .0, "Technical Specification Group Radio Access Network, Medium Access Control (MAC), Protocol Specification (Release 1999)", Jun. 2004, pp. 1-41.

3rd Generation Partnership Project (3GPP), TS 25.321 V4.1.0, "Technical Specification Group Radio Access Network, Medium Access Control (MAC), Protocol Specification (Release 4)", Jun. 2001, pp. 1-44.

3rd Generation Partnership Project (3GPP), TS 25.321 V4.10.0, "Technical Specification Group Radio Access Network, Medium Access Control (MAC) Protocol Specification (Release 4)", Jun. 2004 pp. 1-43.

3rd Generation Partnership Project (3GPP), TS 25.321 V5.13.0, "Technical Specification Group Radio Access Network, MAC Protocol Specification (Release 5)", Mar. 2007, pp. 1-58.

3rd Generation Partnership Project (3GPP), TS 25.321 V5.14.0, "Technical Specification Group Radio Access Network, MAC Protocol Specification (Release 5)", Sep. 2008, pp. 1-58.

3rd Generation Partnership Project (3GPP), TS 25.321 V6.14.0, "Technical Specification Group Radio Access Network, Medium Access Control (MAC), Protocol Specification (3GPP TS 25.321 V6.14.0, (Release 6)", Sep. 2007, pp. 1-94.

3rd Generation Partnership Project (3GPP), TS 25.321 V6.17 .0, "Technical Specification Group Radio Access Network, Medium Access Control (MAC), Protocol Specification (Release 6)", Dec. 2008, pp. 1-95.

(56) References Cited

OTHER PUBLICATIONS

3rd Generation Partnership Project (3GPP), TS 25.321 V7.11.0, "Technical Specification Group Radio Access Network, Medium Access Control (MAC), Protocol Specification (Release 7)", Dec. 2008, pp. 1-147.

3rd Generation Partnership Project (3GPP), TS 25.321 V7.7.0, "Technical Specification Group Radio Access Network, Medium Access Control (MAC), Protocol Specification (Release 7)", Dec. 2007, pp. 1-146.

3rd Generation Partnership Project (3GPP), TS 25.321 V8.0.0, "Technical Specification Group Radio Access Network, Medium Access Control (MAC), Protocol Specification (Release 8)", Dec. 2007, pp. 1-146.

CNIPA, "National Intellectual Property Administration, PRC for Reexamination and Invalidation Examination", Chinese version of the Examination Decision on Request for Invalidation (No. 43196) of Chinese Patent No. 200980108308.5, 020-01-22 00:00:00.0, 15 pages.

CNIPA, "National Intellectual Property Administration, PRC for Reexamination and Invalidation Examination", English Translation of the Examination Decision on Request for Invalidation (No. 43196) of Chinese Patent No. 00980108308.5, 2020-01-22 00:00:00. 0, 13 pages.

Dahlman, et al., "3G Evolution HSPA and LTE for Mobile Broadband", Elsevier Ltd, Academic Press, pp. xxv, 21-122, 157-158, and 170, 2007-01-01 00:00:00.0, 17 pages total.

Jiang et al., "Principle and Performance of Semi-Persistent Scheduling for VoIP in LTE System", International Conference on Wireless Communications, Networking and Mobile Computing, Shanghai, China, Sep. 21-25, 2007, 6 pages.

R.2-080719, "Process ID Allocation for Downlink Persistent Scheduling", CATI, 3GPP TSG RAN WG2 #61, Sorrento, Italy, pp. 1-5.

R.2-081037, "E-UTRA MAC protocol specification update", 3GPP TSG-RAN2 Meeting #61 Sorrento, Italy, 24 pages.

R.2-082311 (Update of R2-081674), "Process ID Allocation for Downlink Persistent Scheduling", CATI, 3GPP TSG RAN WG2 #62, Kansas City, USA, pp. 1-5.

R.2-083363, "DL HARQ Association for Semi-Persistent Scheduling", Alcatel-Lucent, Alcatel Shanghai Bell, 3GPP WSG-RAN WG2 #62bis, Warsaw, Poland, 02 pages.

R.2-083567, "HARQ Process ID's for DL Persistent Scheduling", Norte', 3GPP TSG RAN WG2 #62bis, Warsaw, Poland, pp. 1-5.

R.2-084022, "HARQ Process Id of DL Persistent Scheduling", Huawei, 3GPP TSG-RAN WG2 Meeting #63, Jeju, Korea, 5 pages.

R.2-084098, "Remaining Issues on Persistent Scheduling", Panasonic, 3GPP TSG RAN WG2 #63, Jeju, Korea, 4 pages.

TDOC R2-086175, "Open Issues in Semi Persistent Scheduling", Ericsson, 3GPP TSG-RAN WG2 #64, Prague, Czech Republic, pp. 1-3.

Third Generation Partnership Project (3GPP), "HARQ Process ID's for DL Persistent Scheduling", Nortel, 3GPP TSG RAN WG2 #61, R2-081020, Sorrento, Italy, pp. 1-6.

WQOC R2-080765, "Control of Semi Persistent Scheduling", Ericsson, Samsung, TSG-RAN WG2 Meeting #61, Sorrento, Italy, pp. 1-2.

* cited by examiner

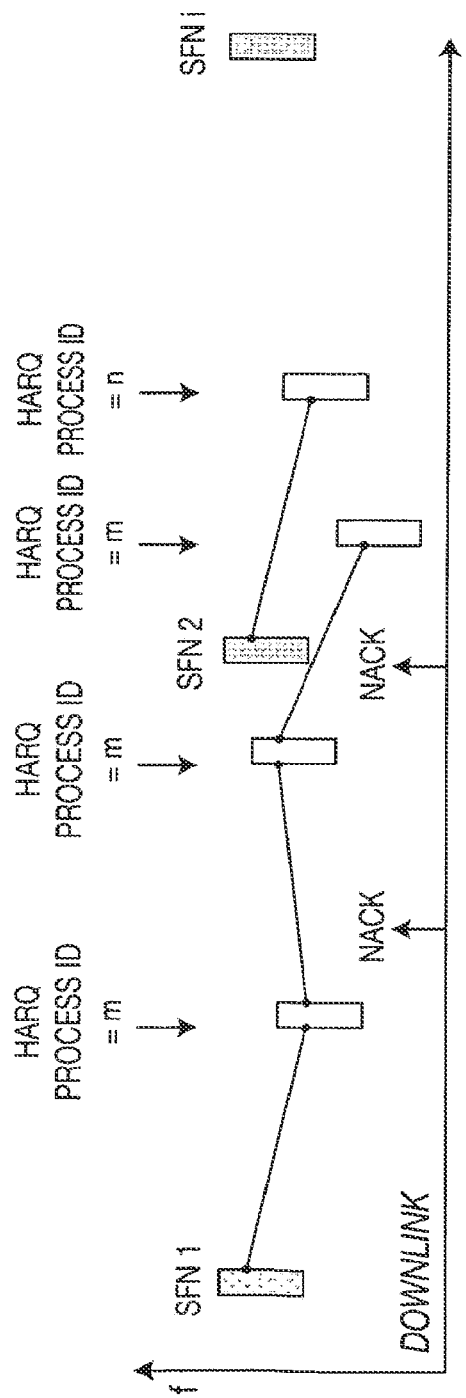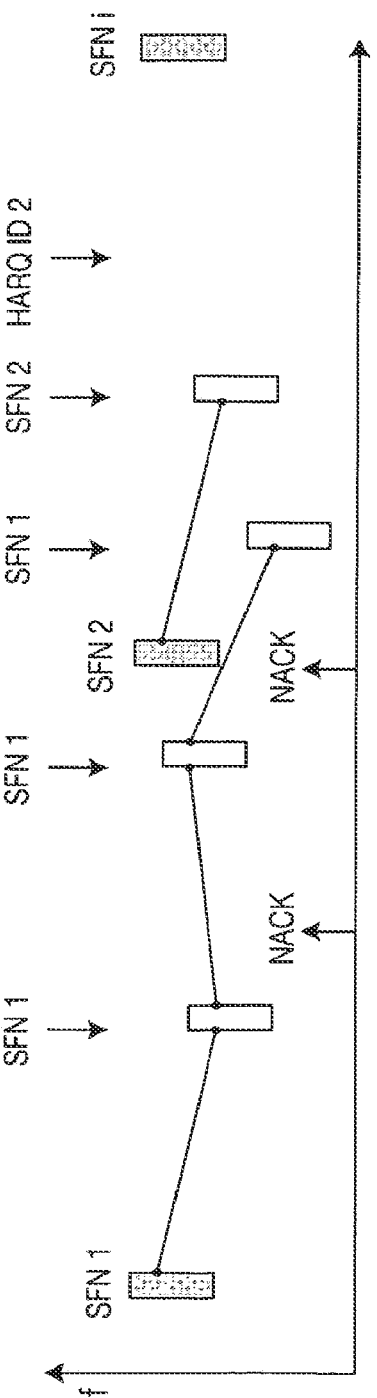

METHOD AND APPARATUS FOR EFFICIENTLY UTILIZING HARQ PROCESSES FOR SEMI-PERSISTENT AND DYNAMIC DATA TRANSMISSIONS

CROSS REFERENCE TO RELATED APPLICATIONS

This application is a continuation of U.S. Non-Provisional application Ser. No. 18/074,223, filed Dec. 2, 2022, which is a continuation of U.S. Non-Provisional application Ser. No. 16/406,826, filed May 8, 2019, which issued as U.S. Pat. No. 11,558,153 on Jan. 17, 2023, which is a continuation of U.S. Non-Provisional application Ser. No. 14/605,562, filed Jan. 26, 2015, which issued as U.S. Pat. No. 10,305,641 on May 28, 2019, which is a continuation of U.S. Non-Provisional application Ser. No. 13/735,494, filed Jan. 7, 2013, which issued as U.S. Pat. No. 8,943,378 on Jan. 27, 2015, which is a continuation of U.S. Non-Provisional application Ser. No. 12/399,174, filed Mar. 6, 2009, which issued as U.S. Pat. No. 8,386,872 on Feb. 26, 2013, which claims the benefit of U.S. Provisional Application No. 61/035,273 filed Mar. 10, 2008, the contents of each of which are incorporated by reference in their entirety herein.

FIELD OF INVENTION

This application is related to wireless communications.

BACKGROUND

The basis for uplink (UL) and downlink (DL) scheduling is dynamic scheduling. In a long term evolution (LTE) wireless communication system, scheduling information is transmitted during transmission timing intervals (TTIs) to a wireless transmit/receive unit (WTRU) via a physical downlink control channel (PDCCH). It has been agreed by radio access network (RAN) working groups (i.e., RAN2) to support semi-persistent scheduling for the DL and the UL in long term evolution (LTE). For semi-persistently scheduled wireless transmit/receive units (WTRUs) in a transmission time interval (TTI), a DL/UL grant does not need to be sent for initial data transmission. The only exception is when an evolved Node-B (eNB) wants to override the persistent resource assignment, which by definition should be infrequent. Otherwise, the sole purpose of a DL/UL persistent resource assignment is lost. As an optimization for voice over Internet protocol (VoIP), persistent scheduling is used for both DL and UL, where the resource for the initial transmissions is persistently allocated and the resources for the hybrid automatic repeat request (HARQ) retransmissions is dynamically allocated.

For the DL, the HARQ Process identification (ID) of a re-transmission must be specified because the same cannot be inferred from the TTI in which the re-transmission occurs, (due to the asynchronous nature of DL re-transmissions). For dynamic scheduling, this is achieved via DL grant signaling. For semi-persistently scheduled WTRUs in a TTI, a DL grant is not sent for initial transmissions, and any subsequent adaptive re-transmissions require a DL grant which explicitly indicates the HARQ Process ID for the re-transmissions.

A solution includes both the WTRU and the eNB to assume that the next available HARQ process-ID is used for a persistently scheduled DL transmission. However, this procedure would not be robust enough in the presence of errors.

When HARQ processes are reserved for persistent transmissions, the HARQ processes left for dynamic transmission are limited. As such, it is not efficient to reserve several HARQ processes only for persistent transmissions if they finish the transmission successfully and cannot be used by other services for a long time.

Therefore, there exists a need for a method to alleviate the above inefficiencies and concerns.

SUMMARY

A method and apparatus are disclosed for efficient HARQ process utilization for semi-persistent and dynamic data transmissions, wherein a reserved HARQ process ID can be reused. A subset of a plurality of HARQ process IDs is reserved to use for a semi-persistent allocation, and data is transmitted based on the semi-persistent allocation. A dynamic allocation is received via a PDCCH. At least one of the reserved HARQ process IDs is selectively used for transmitting data based on the dynamic allocation.

BRIEF DESCRIPTION OF THE DRAWINGS

A more detailed understanding may be had from the following description, given by way of example in conjunction with the accompanying drawings wherein:

FIG. 2 shows an example of a relation between system frame numbers (SFNs) and reserved HARQ process IDs in the downlink;

FIG. 3 shows an example of signaling for persistent retransmission and dynamic allocation.

DETAILED DESCRIPTION

When referred to hereafter, the terminology "wireless transmit/receive unit (WTRU)" includes but is not limited to a user equipment (UE), a mobile station, a fixed or mobile subscriber unit, a pager, a cellular telephone, a personal digital assistant (PDA), a computer, or any other type of user device capable of operating in a wireless environment.

When referred to hereafter, the terminology "evolved Node-B (eNB)" includes but is not limited to a base station, a site controller, an access point (AP), or any other type of interfacing device capable of operating in a wireless environment.

Figure 1:
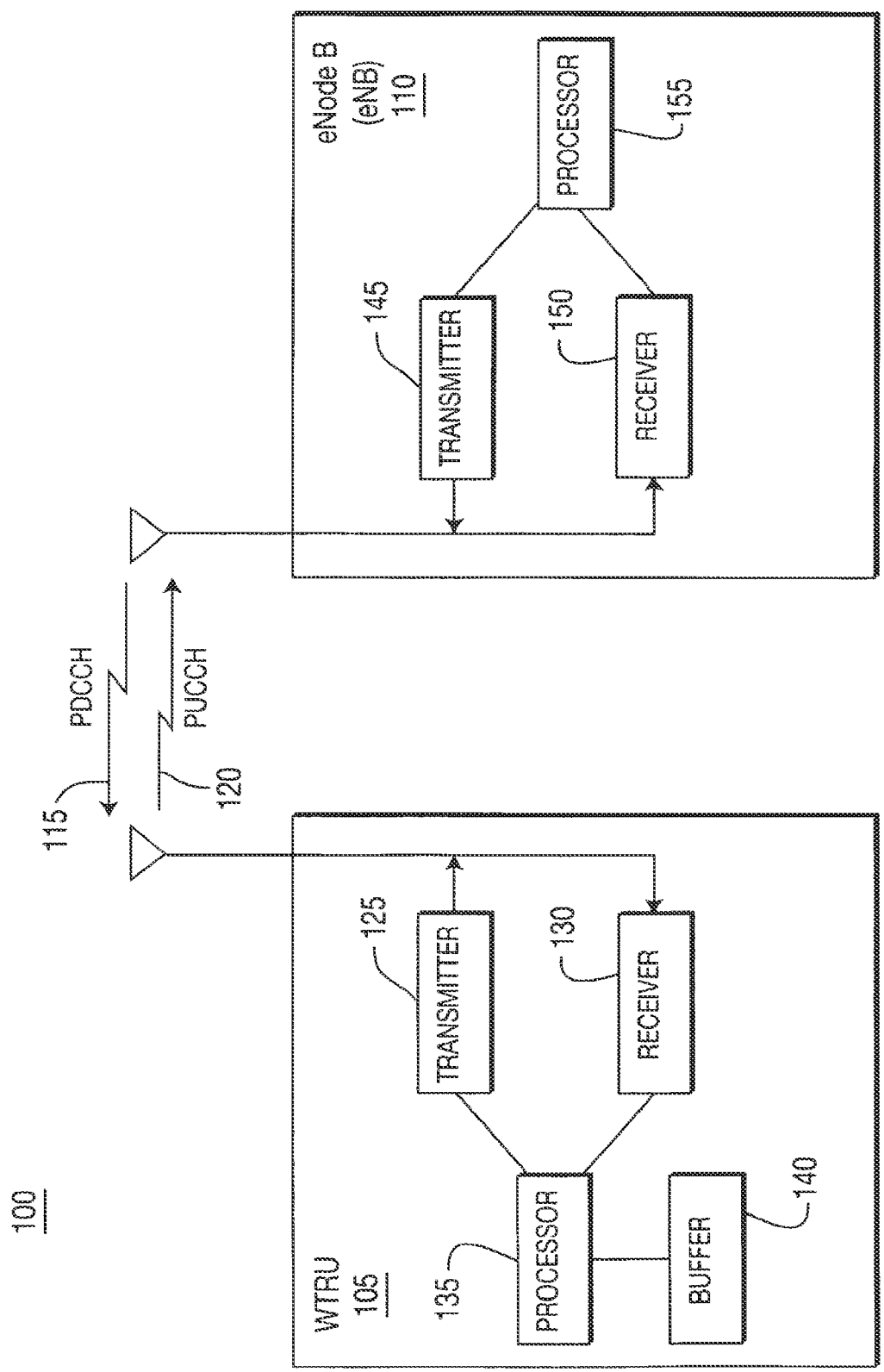
FIG. 1 shows a wireless communication system that is configured to efficiently utilize HARQ processes.

FIG. 1 shows a wireless communication system 100 including a WTRU 105 and an eNB 110, which communicate over a PDCCH 115 and a physical uplink control channel (PUCCH) 120. The WTRU 105 includes a transmitter 125, a receiver 130, a processor 135 and a buffer 140. The eNB 110 includes a transmitter 145, a receiver 150 and a processor 155.

A method is described below for efficiently utilizing DL and UL HARQ resources. In the DL, if a subset of HARQ process IDs are reserved for semi-persistent transmission, the reserved HARQ processes may also be used for dynamic allocation when data associated with a certain reserved HARQ process ID has been successfully transmitted, (i.e., receive an acknowledgement (ACK) from the WTRU 105) and before the reserved HARQ process ID will be used at a next associated system frame number (SFN) moment. For example if one HARQ process m is reserved to associate with an odd SFN, as shown in FIG. 2, and then if a HARQ process m starts transmission at SFN1 and finishes before SFN2, the HARQ process m may be used by dynamic scheduling. In this way, the HARQ process m can be fully utilized without wasting the resource. Also, the dynamic allocation can override the existing HARQ process m such that this process does not finish its transmission.

Alternatively, the dynamic allocation uses the reserved HARQ process when all unreserved HARQ processes are used up, (or are unavailable), and the reserved HARQ process has successfully transmitted the packet or reached the maximum number of retransmissions, or the time is long enough for dynamic allocation and transmission before using this HARQ process ID at the associated SFN for persistent transmission.

Whether to use the reserved HARQ process ID for dynamic scheduling between two associated SFNs using the same reserved HARQ process ID can be signaled in a radio resource control (RRC) message during a persistent allocation setup. For example, it can be put together with reserved HARQ IDs. The configuration may also be signaled in a PDCCH when activating the DL persistent scheduling.

FIG. 2 shows an example whereby HARQ processes are reserved with associated SFNs for DL persistent scheduling. In FIG. 2, SFN1 refers to an odd SFN and SFN2 refers to an even SFN. SFN1 and SFN2 are used here as example to show initial packets to transmit at the odd and even SFN moments. The shaded rectangles represent retransmitted packets. As an example, HARQ processes m and n are reserved for the DL persistent scheduling. The SFN, when the initial transmission is sent, is coupled with the HARQ process ID. As such, when an initial transmission is sent in an odd SFN, the retransmission is sent through the HARQ process m. In accordance with this example shown in FIG. 2, HARQ process n is used when the initial transmission is sent in an even SFN, and the HARQ process m is used for retransmission 3 times. The NACKs in FIG. 2 represent a failed transmission using HARQ process m in the DL failed, whereby the WTRU 105 sends the NACK to the eNB 110, so that eNB 110 will retransmit using HARQ process m.

Still referring to FIG. 2, once one reserved DL HARQ process m has successfully finished DL persistent transmission, for example between two odd SFNs, before the next consecutive odd SFN to use HARQ process m for a new DL persistent transmission, the HARQ process x can be used by the eNB 110 for dynamic scheduling if all unreserved HARQ processes are used up (or are unavailable). Thus, the WTRU 105 may differentiate whether the data from the same HARQ process is for persistent retransmissions or for new dynamic allocation using explicit signaling. The PDCCH signaling can be used for explicitly signaling dynamic scheduling when sharing the reserved HARQ process, for example the HARQ process ID m.

A new data indicator (NDI) in the PDCCH may indicate to the WTRU 105 that this is for new dynamic scheduling if the DL allocation using a reserved HARQ process ID occurs after the WTRU 105 successfully receives the DL persistent data and sends an acknowledgement (ACK) to the eNB 110, or the maximum number of retransmissions has been reached. The WTRU 105 may also determine whether it is a retransmission from a retransmission sequence number (RSN). Also, the DL scheduling grant carried on the PDCCH can use one bit to indicate whether the DL scheduling is for dynamic or persistent allocation.

If the DL dynamic transmission using the reserved HARQ process cannot be successfully received before the next SFN, when this reserved HARQ process has to be used for DL persistent transmission, then any DL dynamic transmission should be suspended and the WTRU 105 should empty the buffer 140 which stores the DL dynamic transmission data using the reserved HARQ process.

At least one transmission time interval (TTI) needs to occur before the reserved HARQ process m for the next immediate associated SFN for a new DL persistent transmission. The buffer 140 stores data for the on-going dynamic transmission associated with the reserved HARQ process m. The buffer 140 should be flushed and parameters for HARQ process m should be reset to the configurations for initial DL persistent transmission.

Alternatively, in addition to reserving a subset of HARQ process IDs for DL persistent transmissions, a subset (preferably more than one) of HARQ process IDs for UL persistent transmissions may also be reserved. The reserved HARQ process IDs for UL persistent transmissions may also be used for UL dynamic transmissions when the reserved HARQ process has finished UL persistent transmission successfully, or has reached the maximum number of retransmissions and there is still time before using the same HARQ process in the next associated SFN for UL persistent transmission. The unreserved HARQ processes for UL dynamic scheduling may be used, and then the reserved HARQ processes are used once the unreserved HARQ processes are all used.

If a subset of HARQ process IDs is to be reserved for UL persistent transmissions, it may be signaled in the RRC during the UL persistent scheduling setup process. As described above for the DL, the configuration of whether to use the reserved HARQ process ID for UL dynamic scheduling between two associated SFNs that use the same reserved HARQ process ID can be signaled in an RRC message during persistent allocation setup. For example, the signaling may be put together with the reserved HARQ IDs. Alternatively, the configuration may be signaled in the PDCCH when activating the UL persistent allocation.

If the WTRU 105 receives an UL grant with a reserved HARQ ID and NDI indicating a new packet before the next associated SFN for UL persistent transmission, then the WTRU 105 realizes that this UL grant is for dynamic scheduling by reusing (or sharing) the reserved HARQ process and the WTRU 105 can start to use that HARQ process and allocated parameter for UL dynamic transmission.

If WTRU 105 detects an ACK, but received an UL grant with the same HARQ process ID indicating a retransmission, then the WTRU 105 knows that a negative acknowledgement (NACK) is detected as an ACK in error and the UL allocation is still for retransmission of the on going UL persistent transmission.

If the WTRU 105 detects a NACK, but the UL grant with a reserved HARQ process ID and NDI indicates a new data packet, then the WTRU 105 knows that the ACK may be detected as a NACK and the new UL grant is for dynamic scheduling before the next SFN and therefore, to use the reserved HARQ process.

If the WTRU 105 does not detect either an ACK or a NACK at the expected time, the WTRU 105 knows the ACK/NACK is lost. If the WTRU 105 later detects an UL grant using the reserved HARQ process with NDI indicating a new data packet, then the WTRU 105 knows the DL ACK is lost and that the reserved HARQ process is used for dynamic scheduling. Otherwise, if the WTRU 105 detects UL grant using a reserved HARQ process ID, but the RSN indicates a retransmission, then the WTRU 105 knows the DL NACK is lost and the allocation is for persistent retransmissions.

If WTRU 105 reserves the HARQ process for UL dynamic transmission, X number of TTIs, for example one (1), before the start of the next SFN to use the same reserved HARQ process t for UL persistent transmission, the WTRU 105 flushes the buffer 140 with the unfinished UL dynamic transmission associated with HARQ process t to prepare for the next UL persistent transmission.

A method for PDCCH signaling for allocation of persistent retransmission and dynamic transmission is disclosed. In accordance with this method, there are multiple ways to signal to the WTRU 105 whether the allocation for retransmissions is for the same initial transmission to avoid the ambiguity at the WTRU 105. If the HARQ process ID along with the RSN is included in the DL allocation for retransmission of persistent scheduling, it is possible to avoid ambiguity at WTRU 105 without reserving a subset of HARQ processes for persistent scheduling.

The SFNs may be used for persistent allocation for transmission and retransmissions (DL/UL), and HARQ IDs may be used for dynamic allocation for initial transmissions and retransmissions. When making resource allocation for retransmissions, only the HARQ process ID is included in the PDCCH for dynamic allocation. As such, there is no HARQ process ID in the PDCCH for persistent transmission. When the eNB 110 makes a DL or UL resource allocation, the eNB 110 cannot use the same HARQ process for any unfinished dynamic and persistent transmissions. In that way, the WTRU 105 is able to know if the DL or UL allocation is for dynamic and persistent transmissions.

Using SFNs for persistent allocation can differentiate between different persistent transmission periods. FIG. 3 illustrates an example operation using the SFN and a HARQ ID for persistent and dynamic allocation. For example, when retransmission for initial persistent transmission occurs after SFN2, if SFN1 is used in persistent allocation for retransmission of SFN1 packet based on the RSN value in signaling, then the WTRU 105 will have no ambiguity to differentiate whether to combine the allocation with the SFN1 or SFN2 packets.

When reserved the HARQ ID is received by the WTRU 105 for resource allocation, the WTRU 105 knows that the reserved HARQ process has already finished its persistent transmission and can be used for dynamic allocation. For example, in FIG. 3, once HARQ ID 2, (assuming that it is mapped to SFN2), has successfully finished the persistent transmissions, then HARQ ID 2 may be used for dynamic allocation and, if the WTRU 105 decodes HARQ ID 2 in the resource allocation, then the WTRU 105 knows this HARQ process is used for dynamic allocation. Although the PDCCH 115 is used in this example, the same principle holds true also for the PUCCH 120.

It is preferable that the activation time for persistent transmission is long enough to allow the eNB 110 to realize whether activation signaling included in the PDCCH has been successfully decoded by the WTRU 105 or not. To make sure the PDCCH for DL/UL persistent scheduling activation is successfully received by the WTRU 105, an ACK/NACK may be sent by the WTRU 105 for persistent activation signaling to the eNB 110, so that eNB 110 can retransmit persistent activation signaling for a synchronized DL or UL persistent transmission. The allocation of UL ACK/NACK resources should be predetermined if this mechanism is going to be used.

Referring again to FIG. 1, the WTRU 105 controls the allocation of HARQ resources. The processor 135 is configured to reserve a subset of a plurality of HARQ process IDs to use for a semi-persistent allocation. The receiver is configured to receive a dynamic allocation via the DL PDCCH. The transmitter 125 is configured to transmit data based on the semi-persistent allocation, and selectively use at least one of the reserved HARQ process IDs for transmitting data based on the dynamic allocation.

A HARQ process associated with at least one of the reserved HARQ process IDs may be used over a time period between two different SFN moments to transmit data. When data associated with the at least one reserved HARQ process ID was previously transmitted, the reserved HARQ process ID may not be used until a next associated SFN moment. The reserved HARQ process IDs may be used after all unreserved HARQ process IDs have been used. The reserved HARQ process IDs may be used by higher priority services. The reserved HARQ process IDs may be included in an RRC message.

Figure 4:
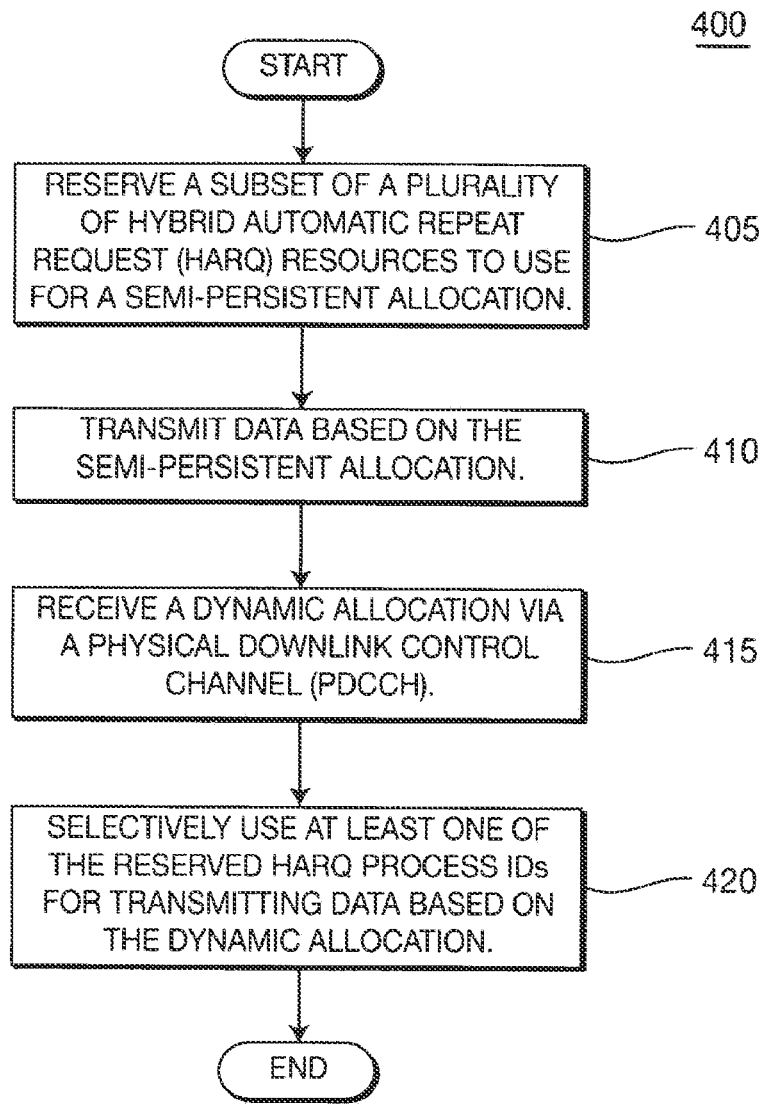
FIG. 4 is a flow diagram of a procedure for efficiently utilizing HARQ processes for semi-persistent and dynamic data transmissions.

FIG. 4 is a flow diagram of a procedure 400 for efficiently utilizing HARQ processes for semi-persistent and dynamic data transmissions. In step 405, a subset of a plurality of HARQ resources is reserved to use for a semi-persistent allocation. In step 410, data is transmitted based on the semi-persistent allocation. In step 415, a dynamic allocation is received via a DL PDCCH. In step 420, at least one of the reserved HARQ process IDs is selectively used for transmitting data based on the dynamic allocation.

Although features and elements are described above in particular combinations, each feature or element can be used alone without the other features and elements or in various combinations with or without other features and elements. The methods or flow charts provided herein may be implemented in a computer program, software, or firmware incorporated in a computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine.

A processor in association with software may be used to implement a radio frequency transceiver for use in a wireless transmit receive unit (WTRU), user equipment (UE), terminal, base station, radio network controller (RNC), or any host computer. The WTRU may be used in conjunction with modules, implemented in hardware and/or software, such as a camera, a video camera module, a videophone, a speakerphone, a vibration device, a speaker, a microphone, a television transceiver, a hands free headset, a keyboard, a Bluetooth® module, a frequency modulated (FM) radio unit, a liquid crystal display (LCD) display unit, an organic light-emitting diode (OLED) display unit, a digital music player, a media player, a video game player module, an Internet browser, and/or any wireless local area network (WLAN) or Ultra Wide Band (UWB) module.

What is claimed is:

1. A method implemented by a wireless transmit/receive unit (WTRU), the method comprising:
receiving a radio resource control (RRC) message, the RRC message including configuration information that indicates one or more uplink hybrid automatic repeat request (HARQ) process identifications (IDs) for use with an uplink semi-persistent resource;
determining a first uplink HARQ process ID for a first uplink transmission sent using the uplink semi-persistent resource, wherein the first uplink HARQ process ID is one of the one or more uplink HARQ process IDs configured for use with the uplink semi-persistent resource, and the first uplink HARQ process ID is determined based at least in part on a system frame number (SFN) associated with the first uplink transmission;
receiving a physical downlink control channel (PDCCH) transmission, the PDCCH transmission comprising a grant for a dynamic uplink transmission associated with the first uplink HARQ process ID;
determining that the WTRU has not successfully completed transmission of data sent via the dynamic uplink transmission prior to performing a second uplink transmission associated with the uplink semi-persistent resource using the first HARQ process ID; and
flushing a buffer of the data associated with the dynamic uplink transmission based on performing the second uplink transmission associated with the uplink semi-persistent resource using the first HARQ process ID.

2. The method of claim 1, wherein the PDCCH transmission comprises an explicit indication of the first uplink HARQ process ID.

3. The method of claim 1, wherein the PDCCH transmission comprising the grant for the dynamic uplink transmission associated with the first uplink HARQ process ID is received prior to the WTRU successfully completing transmission of data associated with the first uplink transmission, and the method further comprising the WTRU flushing a buffer of the data associated with the first uplink transmission based on receiving the PDCCH transmission comprising the grant for the dynamic uplink transmission associated with the first uplink HARQ process ID.

4. The method of claim 1, wherein the configuration information indicates one or more downlink HARQ process IDs for use with a downlink semi-persistent resource.

5. The method of claim 4, further comprising receiving a second PDCCH transmission, the second PDCCH transmission indicating activation of the downlink semi-persistent resource.

6. The method of claim 5, further comprising transmitting an acknowledgement indicating receipt of the second PDCCH transmission that indicates activation of the downlink semi-persistent resource.

7. The method of claim 1, further comprising:
receiving an acknowledgment indicating receipt of data in the first uplink transmission.

8. The method of claim 1, further comprising suspending processing of data associated with the dynamic uplink transmission based on performing the second uplink transmission associated with the uplink semi-persistent resource using the first HARQ process ID prior to receiving an acknowledgement of successful transmission of the data associated with the dynamic uplink transmission, wherein suspending processing of data comprises flushing the buffer of data.

9. A wireless transmit/receive unit (WTRU) comprising a processor and memory, the processor and memory configured to:
receive a radio resource control (RRC) message, the RRC message including configuration information that indicates one or more uplink hybrid automatic repeat request (HARQ) process identifications (IDs) for use with an uplink semi-persistent resource;
determine a first uplink HARQ process ID for a first uplink transmission sent using the uplink semi-persistent resource, wherein the first uplink HARQ process ID is one of the one or more uplink HARQ process IDs configured for use with the uplink semi-persistent resource, and the first uplink HARQ process ID is determined based at least in part on a system frame number (SFN) associated with the first uplink transmission;
receive a physical downlink control channel (PDCCH) transmission, the PDCCH transmission comprising a grant for a dynamic uplink transmission associated with the first uplink HARQ process ID;
determine that the WTRU has not successfully completed transmission of data sent via the dynamic uplink transmission prior to performing a second uplink transmission associated with the uplink semi-persistent resource using the first HARQ process ID; and
flush a buffer of the data associated with the dynamic uplink transmission based on performing the second uplink transmission associated with the uplink semi-persistent resource using the first HARQ process ID.

10. The WTRU of claim 9, wherein the PDCCH transmission comprises an explicit indication of the first uplink HARQ process ID.

11. The WTRU of claim 9, wherein the PDCCH transmission comprising the grant for the dynamic uplink transmission associated with the first uplink HARQ process ID is received prior to the WTRU successfully completing transmission of data associated with the first uplink transmission, and the processor and memory are further configured to flush a buffer of the data associated with the first uplink transmission based on receiving the PDCCH transmission comprising the grant for the dynamic uplink transmission associated with the first uplink HARQ process ID.

12. The WTRU of claim 9, wherein the configuration information indicates one or more downlink HARQ process IDs for use with a downlink semi-persistent resource.

13. The WTRU of claim 12, further comprising receiving a second PDCCH transmission, the second PDCCH transmission indicating activation of the downlink semi-persistent resource.

14. The WTRU of claim 13, wherein the processor and memory are further configured to transmit an acknowledgement indicating receipt of the second PDCCH transmission that indicates activation of the downlink semi-persistent resource.

15. The WTRU of claim 9, wherein the processor and memory are further configured to receive an acknowledgment indicating receipt of data in the first uplink transmission.

16. The WTRU of claim 9, wherein the processor and memory are further configured to suspend processing of data associated with the dynamic uplink transmission based on performing the second uplink transmission associated with the uplink semi-persistent resource using the first HARQ process ID prior to receiving an acknowledgement of successful transmission of the data associated with the dynamic uplink transmission, wherein the processor and memory being configured to suspend processing of data comprises the processor and memory configured to flush the buffer of data.

17. A base station comprising:
a transceiver; and
a processor, the processor configured to:
send, via the transceiver, a radio resource control (RRC) message, the RRC message including configuration information that indicates one or more uplink hybrid automatic repeat request (HARQ) process identifications (IDs) for use with an uplink semi-persistent resource, wherein the uplink semi-persistent resource is used to determine a first uplink HARQ process ID for a first uplink transmission sent, wherein the first uplink HARQ process ID is one of the one or more uplink process IDs configured for use with the semi-persistent resource, and the first uplink HARQ process ID is determined based at least in part on a system frame number (SFN) associated with the first uplink transmission;
send, via the transceiver, a physical downlink control channel (PDCCH) transmission, the PDCCH transmission comprising a grant for a dynamic uplink transmission associated with a first uplink HARQ process ID; and
receive a second uplink transmission associated with the uplink semi-persistent resource prior to sending an acknowledgement of successful transmission of data associated with the dynamic uplink transmission.

18. The base station of claim 17, wherein the PDCCH transmission comprises an explicit indication of the first uplink HARQ process ID.

19. The base station of claim 18, further comprising sending a second PDCCH transmission, the second PDCCH transmission indicating activation of the downlink semi-persistent resources.

20. The base station of claim 17, wherein the configuration information indicates one or more downlink HARQ process IDs for use with a downlink semi-persistent resource.

* * * * *

UNITED STATES PATENT AND TRADEMARK OFFICE
CERTIFICATE OF CORRECTION

PATENT NO. : 12,284,044 B2  
APPLICATION NO. : 18/531061  
DATED : April 22, 2025  
INVENTOR(S) : Jin Wang and Guodong Zhang Page 1 of 1

It is certified that error appears in the above-identified patent and that said Letters Patent is hereby corrected as shown below:

In the Claims

In Claim 17: Column 9, Line 4, delete "Abase", and insert -- A base --.

Signed and Sealed this
Eighth Day of July, 2025

Coke Morgan Stewart
*Acting Director of the United States Patent and Trademark Office*